US011974569B2

(12) United States Patent
Gain et al.

(10) Patent No.: US 11,974,569 B2
(45) Date of Patent: May 7, 2024

(54) DEVICE FOR HOLDING CORNEAL TISSUE FOR PHOTONIC TREATMENT THEREOF

(71) Applicants: UNIVERSITÉ JEAN MONNET SAINT ETIENNE, Saint Etienne (FR); CENTRE NATIONAL DE LA RECHERCHE SCIENTIFIQUE, Paris (FR); CENTRE HOSPITALIER UNIVERSITAIRE, Saint Etienne (FR); MANUTECH-USD, Saint Etienne (FR)

(72) Inventors: Philippe Gain, Lyons (FR); Gilles Thuret, Saint Bonnet les Oules (FR); Cyril Mauclair, Saint Etienne (FR); Clotilde Jumelle, Fresnoy en Gohelle (FR); Gregory Egaud, Jonzieux (FR)

(73) Assignees: UNIVERSITE JEAN MONNET, Saint Etienne (FR); CENTRE NATIONAL DE LA RECHERCHE SCIENTIFIQUE, Paris (FR); CENTRE HOSPITALIER UNIVERSITAIRE, Saint Etienne (FR); MANUTECH-USD, Saint Etienne (FR)

( * ) Notice: Subject to any disclaimer, the term of this patent is extended or adjusted under 35 U.S.C. 154(b) by 487 days.

(21) Appl. No.: 17/261,107

(22) PCT Filed: Jul. 17, 2019

(86) PCT No.: PCT/EP2019/069192
§ 371 (c)(1),
(2) Date: Jan. 18, 2021

(87) PCT Pub. No.: WO2020/016270
PCT Pub. Date: Jan. 23, 2020

(65) Prior Publication Data
US 2021/0321607 A1 Oct. 21, 2021

(30) Foreign Application Priority Data
Jul. 17, 2018 (FR) ...................................... 1870835

(51) Int. Cl.
A01N 1/02 (2006.01)
A61L 27/36 (2006.01)

(52) U.S. Cl.
CPC ........ A01N 1/0263 (2013.01); A61L 27/3691 (2013.01); A61L 2430/16 (2013.01)

(58) Field of Classification Search
CPC .................................................. A01N 1/0263
See application file for complete search history.

(56) References Cited

U.S. PATENT DOCUMENTS

2008/0140434 A1 11/2008 Krolman
2008/0294149 A1 11/2008 Krolman
(Continued)

FOREIGN PATENT DOCUMENTS

WO 2014/140434 A1 9/2014

OTHER PUBLICATIONS

Guindolet et al., "Storage of Porcine Cornea in an Innovative Bioreactor", Investigative Ophthalmology & Visual Science, Nov. 2017, vol. 58, No. 13, pp. 5907-5917.

Primary Examiner — Jonathan M Hurst
(74) Attorney, Agent, or Firm — BCF LLP

(57) ABSTRACT

The present invention relates to a device for holding human or animal corneal tissue previously removed for photon treatment thereof with electromagnetic radiation, notable in that the holding device comprises: a stack of elements along a longitudinal axis (A-A') of the device, said stack comprising: a first plate (1) that is transparent to the electromagnetic radiation, a peripheral seal (4) positioned on the first plate (1), the peripheral seal (4) being intended to extend around the corneal tissue (6), a second plate (2) that is transparent (Continued)

to the electromagnetic radiation on the peripheral seal (4), an immobilizing system (51, 52) for immobilizing the stack of elements and able to press the first and second plates (1, 2) firmly against the corneal tissue in order to apply mechanical stress to the anterior and posterior faces of the corneal tissue.

14 Claims, 3 Drawing Sheets

(56) References Cited

U.S. PATENT DOCUMENTS

| | | | |
|---|---|---|---|
| 2016/0029618 A1* | 2/2016 | Gain | A01N 1/0247 435/284.1 |
| 2017/0027754 A1 | 2/2017 | Muller | |
| 2017/0319329 A1 | 11/2017 | Muller et al. | |

\* cited by examiner

DEVICE FOR HOLDING CORNEAL TISSUE FOR PHOTONIC TREATMENT THEREOF

CROSS-REFERENCE TO RELATED APPLICATIONS

This application is a national phase filing under 35 U.S.C. § 371 of International Application No. PCT/EP2019/069192 filed on Jul. 17, 2019, which claims benefit of priority from French Patent Application No. 1870835 filed Jul. 17, 2018, the contents of which are hereby incorporated by reference in their entirety.

FIELD OF THE INVENTION

The present invention relates to the general technical field of medical devices for the treatment and/or cutting of ex vivo human or animal corneal tissue.

Such a device can be used to perform experiments on the cornea and/or to cut/treat a cornea for purposes of transplantation.

BACKGROUND OF THE INVENTION

The cornea is an essential element of a patient's vision: indeed, it constitutes the window through which images of the outside world enter the eye.

A patient's cornea can suffer various types of damage—causing total or partial loss of vision—related to different conditions from which patient suffers, such as corneal dystrophy, keratoconus, or opacity or perforation resulting from corneal infection.

When the cornea has become opaque, deformed or perforated, the patient is likely to benefit from a transplant. This graft can be total or partial, and of different shapes.

Furthermore, it is now possible to modify the dioptric power of the cornea by inserting therein a graft in the form of a lenticule of chosen shape. It is also possible to insert a very thin corneal lamina covered with endothelial cells for purposes of an endothelial graft (corneal bioengineering).

Partial corneal transplantation is the grafting of a piece of healthy cornea from a donor—or corneal implant—to replace a portion of the recipient's diseased cornea.

In order to prepare the corneal implant to be grafted, various cutting devices have already been proposed.

The document US 2017/319329 describes in particular a system for forming corneal implants including a first cutting apparatus and a second cutting apparatus.

The first cutting apparatus is configured to cut a cornea from a donor and form a portion of cornea. More precisely, the first cutting apparatus is configured to cut the donor cornea along an axis extending between an anterior surface and a posterior surface of the cornea.

The second cutting apparatus is configured to form a plurality of lenticules from the portion of cornea by forming a series of transverse cuts in the portion of cornea. Corneal tissue between two consecutive cutting planes constitutes a lenticule. This lenticule is then used to form the corneal implant.

The second cutting apparatus consists of a housing including:
  a bottom,
  side walls,
  a window transparent to light radiation opposite to the bottom.

The housing also comprises a chamber for receiving the portion of cornea to be cut into lenticules. An air flow passes through the housing between the transparent window and the chamber, and a moisturizing fluid circulates in the housing between its bottom and the chamber in order to keep the posterior surface of the cornea immersed in the fluid.

As the portion of cornea is not mechanically constrained between its anterior and posterior surfaces, it is relaxed. To create the cutting planes, the transparent window is movable in translation in a direction perpendicular to the bottom to allow the portion of cornea to be flattened from the front prior to creating the cutting planes using laser radiation.

A disadvantage of this type of device is that it does not allow the creation of accurate cutting planes. Indeed, the portion of cornea may undergo antero-posterior displacements, particularly during the laser/cornea interaction, which is detrimental to the focusing accuracy of the laser beam.

Another disadvantage of this type of device is that the quality of the cutting planes decreases with depth. Indeed, the deeper the focal plane is in the cornea, the more the efficiency of the laser beam decreases. Furthermore, the number of lenticules that can be created with this type of device is limited.

Yet another disadvantage of this type of device is that the receiving chamber of the portion of cornea is not enclosed (cornea in a non-sealed environment). The device must therefore be handled in a controlled environment (microbiological safety station, clean room, operating theatre).

The document WO2014/140434 describes a device for storing a corneal specimen comprising an endothelial lid, an epithelial lid, an intermediate component between the endothelial and epithelial lids, and a locking system. In the device according to WO2014/140434, the portion of cornea is not mechanically constrained between its anterior and posterior surfaces. This storage device is further unsuitable for the formation of corneal implants by cutting the portion of cornea.

The document US 2008/294149 describes an observation chamber for preserving corneal tissue. The chamber comprises a container and a lid. The container comprises a corneal basket formed by a plurality of prongs to support the corneal tissue. The prongs are sized to accommodate corneas of different sizes. In the device according to US 2008/294149, the portion of cornea is not mechanically constrained between its anterior and posterior surfaces. This storage device is further unsuitable for the formation of corneal implants by cutting the portion of cornea.

A purpose of the present invention is to propose a device for holding corneal tissue for treatment and/or cutting which overcomes at least one of the above-mentioned disadvantages.

BRIEF DESCRIPTION OF THE INVENTION

To this end, the invention proposes a device for holding human or animal corneal tissue previously removed for photonic treatment from electromagnetic radiation, remarkable in that the holding device comprises:
  a stack of elements along a longitudinal axis A-A' of the device, said stack comprising:
    a first plate transparent to electromagnetic radiation,
    a peripheral seal positioned on the first plate, the peripheral seal being intended to extend around the corneal tissue (without necessarily being in contact with the corneal tissue),
    a second plate transparent to electromagnetic radiation on the peripheral seal, a locking system for the stack of elements capable of pressing the first and second plates against the corneal tissue to apply mechanical stress to the anterior and posterior surfaces of the corneal tissue.

The device described above allows a cornea to be treated/cut under sterile conditions.

By working the cornea from both surfaces, the device according to the invention allows to limit the power of the laser beam necessary when forming fragments from the cornea. Since half the cuts are made through one surface and the second half through the opposite surface, the laser beam has a maximum of only half of the cornea to pass through. Less energy is thus used and the tissue does not deteriorate, which improves the quality of the fragment.

Furthermore, the mechanical stress applied by the first and second plates to the anterior and posterior surfaces of the corneal tissue allows to limit the risks of anterior-posterior displacement of the corneal tissue during application of the electromagnetic beam, in particular during the interaction between the photonic beam and the corneal tissue. This mechanical stress also makes it possible to create a finer and more precise cutting plane by forcing the bubbles created by the beam to evacuate from the tissue. This reduces the thickness of the fragments and consequently increases the number of implants that can be created in the same cornea.

These cut fragments are intended to be used for various applications: in vitro reconstruction of endothelial grafts; patch for reconstructive surgery; intra-corneal implant to modify the refractive properties of the cornea, etc. An example of the use of the invention is the cutting of multiple lamellae (up to 20) in a single cornea by femtosecond laser. Such a number of lamellae has never been obtained with the devices of the prior art.

Preferred but non-limiting aspects of the device according to the invention are the following:
- the first and second plates can be parallel, the distance between the first and second plates being comprised between 100 μm and 1800 μm, preferably between 400 μm and 1500 μm, and more preferably between 500 μm and 700 μm,
- the thickness of the peripheral seal may be comprised between 100 μm and 1800 μm, preferably between 400 μm and 1500 μm, and more preferably between 500 μm and 700 μm, said seal thickness defining the distance between the first and second plates representative of the mechanical stress applied to the corneal tissue by said plates,
- the locking system for the stack of elements may be capable of pressing the first and second plates against the peripheral seal so as to space the first and second plates at a distance comprised between 100 μm and 1800 μm, preferably between 400 μm and 1500 μm, and more preferably between 500 μm and 700 μm,
- the locking system may include a frame intended to at least partially surround the edges of the first and second plates, the frame being able to:
  - induce on the first plate the application of a force parallel to the longitudinal axis and tending to move the first plate toward the second plate,
  - induce on the second plate the application of a force parallel to the longitudinal axis and tending to move the second plate toward the first plate,
- the frame can be composed of at least a first and second portion, each portion including an upper tray, a lower tray and a side wall between the upper and lower trays:
  - the inner face of the upper tray being intended to come facing the outer face of the first plate,
  - the inner face of the lower tray being intended to come facing the outer face of the second plate, and
  - the inner face of the side wall being intended to come facing the edges of the plates and the outer face of the seal,
- the locking system may further comprise at least one clamping element, such as a screw, each clamping element being intended to cooperate with a respective hole provided in the upper and/or lower tray of a portion of the frame,
- each clamping element can be movable to adjust the distance between the first and second plates, said distance being comprised between 100 μm and 1800 μm, preferably between 400 μm and 1500 μm, and more preferably between 500 μm and 700 μm,
- the first and second portions of frame include fastening means to enable said portions to be joined together,
- the device may further comprise a spacer positioned between the first and second plates, the peripheral seal extending around the spacer,
- the thickness of the spacer may be comprised between 100 μm and 1800 μm, preferably between 400 μm and 1500 μm, and more preferably between 500 μm and 700 μm, said thickness of the spacer defining the distance between the first and second plates representative of the mechanical stress applied to the corneal tissue by said plates, said distance being comprised between 100 μm and 1800 μm, preferably between 400 μm and 1500 μm, and more preferably between 500 μm and 700 μm,
- the spacer may have at least one main opening defining, together with the inner faces of the first and second plates, a housing intended to contain the corneal tissue,
- the spacer may have at least one degassing compartment,
- the spacer may have at least one connecting channel extending between the main opening and the degassing compartment for the delivery of gas bubbles formed in the corneal tissue.

BRIEF DESCRIPTION OF THE DRAWINGS

Other features and advantages of the device according to the invention will be more apparent from the following description of several variants of execution, given by way of non-limiting examples, from the appended drawings on which.

DETAILED DESCRIPTION OF THE INVENTION

Various examples of a corneal tissue holding device will now be described with reference to the figures. In these different figures, the equivalent elements are designated by the same numerical reference.

In the remainder of the description, the holding device according to the invention will be presented with reference to the cutting of corneal tissue (i.e. a cornea or part of a cornea such as a central disc previously trephined), it being understood that the use of the device is not limited to the cutting of corneal fragments.

In particular, the device described hereinbelow can be used to carry out a photonic treatment of corneal tissue, such as cross-linking of collagen by a light-activated photosensitizing agent (for example riboflavin and UVA), in order to modify its biomechanical properties (hardening). The reader will appreciate that cross-linking can also be carried out in the device using a chemical agent outside of any electromagnetic radiation (the interest of the device then being to cross-link the cornea under stress conditions and then to cut it in the same device without having to decondition it in the meantime).

1. General Points

Figure 1:
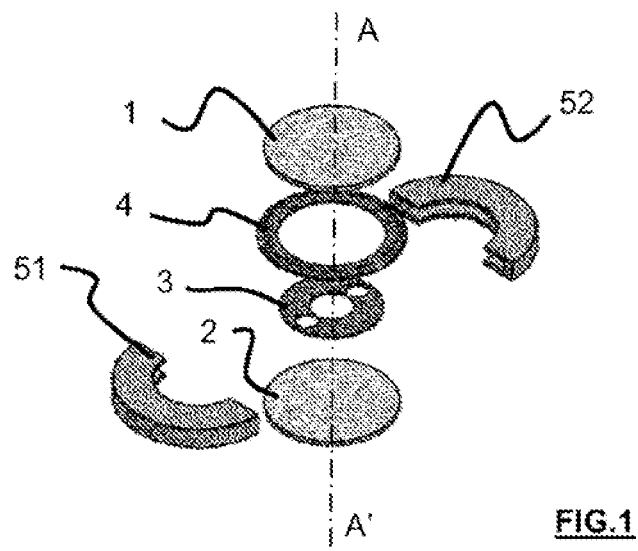
FIG. 1 is an exploded perspective view of the corneal tissue holding device.
Figure 2:
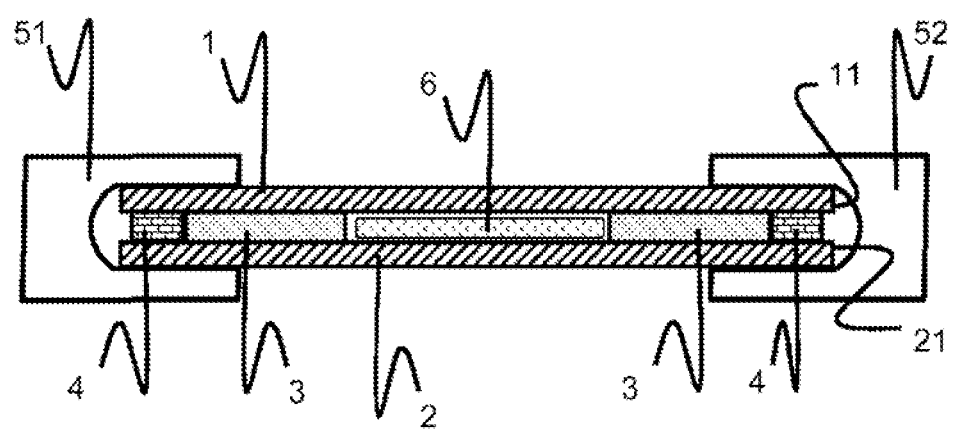
FIG. 2 is a sectional view of the holding device once assembled.

With reference to FIGS. 1 and 2, an example of a corneal tissue holding device according to the invention has been illustrated.

The device comprises:
- first and second plates 1, 2 transparent to electromagnetic radiation,
- optionally a spacer 3 intended to be positioned between the first and second plates 1, 2,
- a peripheral seal 4 intended to be positioned between the first and second plates, the peripheral seal extending around the spacer,
- a locking system for the assembly of the plates 1, 2, the spacer 3 and the peripheral seal 4.

1.1. Transparent Plates

Each plate 1, 2 is made of one (or more) biocompatible material(s) that can be sterilized and is (are) transparent to electromagnetic radiation emitted by a radiation source—such as a laser (an acronym for light amplification by stimulated emission of radiation) or any other type of radiation source known to the person skilled in the art for the treatment of corneal tissue.

In the embodiment shown in FIG. 1, each plate 1, 2 is made of a single material, such as glass or poly(methyl methacrylate) or any other material known to the skilled person.

In certain variant embodiments, each plate 1, 2 can be composed of a superimposition of layers of different materials. For example, in a variant embodiment, each plate 1, 2 is composed of a layer of rigid material (such as glass) extending between two layers of flexible material (for example silicone-based):
- the layer of rigid material increases the mechanical strength of the plate 1, 2, while
- the layers of flexible material allow to limit the risks of dispersion of pieces of the layer of rigid material in case of breakage of the latter.

Each plate 1, 2 can also comprise reinforcements to increase its mechanical strength. The reinforcements extend for example to the edges 11, 21 of the plate 1, 2. The reinforcements can consist of rods of rigid material—such as titanium or stainless steel or any other biocompatible metal known to the skilled person—embedded in the plate 1, 2.

In a variant, the reinforcements can be in the same material as the plate 1, 2. For example, the reinforcements may consist of one (or more) peripheral zone(s) of the plate 1, 2 having a thickness (or thicknesses) greater than the thickness of a central zone of the plate 1, 2. Thus, the plate 1, 2 may comprise thicker zones to increase its mechanical strength and thinner zones for better transmission of electromagnetic radiation.

Each plate 1, 2 may lie substantially in one plane or be concave/convex, the curvature (or absence of curvature) of each plate 1, 2 depending on the intended application. In all cases, the first and second plates are intended to extend parallel to each other. In the context of the present invention, "parallel flat/concave/convex plates" means plates the spacing of which is constant at all points. Thus, the distance between the first and second plates is constant, and comprised between 100 µm and 1800 µm, preferably between 400 µm and 1500 µm, and more preferably between 500 µm and 700 µm. This allows the anterior and posterior surfaces of the corneal tissue 6 to be mechanically stressed to ensure that it is locked in position in the holding device.

In the embodiment shown in FIG. 1, each plate 1, 2 is circular in shape. However, it is quite obvious to the skilled person that other shapes can be envisaged for each plate 1, 2 (square, rectangular, triangular, etc.).

1.2. Spacer

The spacer 3 is an intermediate component intended to be positioned between the first and second plates 1, 2. It enables a predefined distance between the first and second plates 1, 2 to be maintained.

The spacer has several functions:
- it limits the XY displacement of corneal tissue (XY being the plane perpendicular to a longitudinal axis A-A' of the device)
- it allows an easy location of its position by electromagnetic radiation treatment instruments,
- it imposes the distance between the 2 plates in case where the (simple) system does not have a micrometric screw to adjust the spacing between the plates.

The spacer 3 is preferably rigid. However, the spacer 3 can also be elastically deformable. The spacer 3 is for example made of a biocompatible and sterilizable material, in particular silicone-based.

Figure 4A:
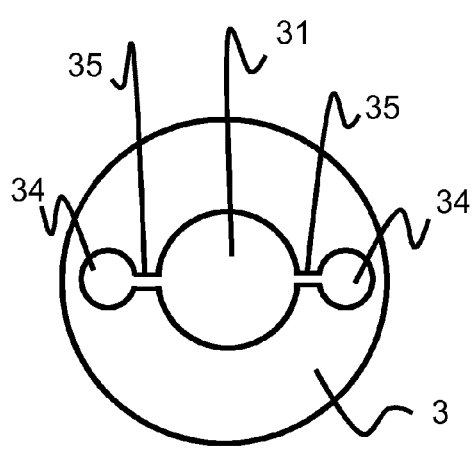

In the embodiment shown in FIG. 4A, the spacer 3 comprises a main opening 31. The central opening can be circular or any other desired shape depending on the application (square, rectangular, etc.). The side wall of the main opening 31 defines, together with the inner surfaces of the first and second plates 1, 2, a housing intended to contain a corneal tissue 6.

Figure 4B:
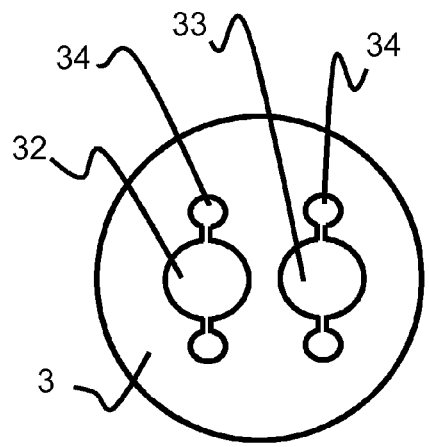

In a variant and as shown in FIG. 4B, the spacer 3 may comprise a plurality of main openings 32, 33. In this case, each main opening 32, 33 is intended to receive a respective corneal tissue 6. Thus, the holding device may comprise a plurality of housings each intended to hold a respective corneal tissue 6.

Preferably, the main opening 31, 32, 33 (or each opening) is circular, the diameter of the opening being substantially equal to the diameter of the corneal tissue 6 to laterally constrain the latter.

Advantageously, the spacer 3 can also comprise one (or more) degassing compartment(s) 34. This (or these) degassing compartment(s) 34 allow(s) storage of gas bubbles formed in the corneal tissue 6 during the application of electromagnetic radiation for purposes of cutting. Indeed, to cut a fragment of corneal tissue, an electromagnetic beam generated by a femtosecond laser (delivering ultra-short, high-powered pulses) can be used (or any other laser known to the skilled person, for example a so-called "excimer" UV laser). At each pulse, the femtosecond laser generates a beam. This beam is focused (at a so-called "focusing" point) located in the corneal tissue 6. A gas bubble is formed at the focusing point, causing a very localized disruption of the surrounding tissue. To form a cutting plane in the corneal tissue 6, a succession of small adjacent gas bubbles is generated by moving the beam. Thus, gas bubbles are formed in the corneal tissue 6 during the formation of a fragment. The degassing compartment(s) 34 allow(s) storage of these gas bubbles outside the corneal tissue 6.

Each compartment 34 may be connected to one (or more) main opening(s) 31, 32, 33 via one (or more) connecting channel(s) 35. This (or these) channel(s) 35 allow(s) the gas bubbles formed in the corneal tissue 6 to be delivered to the degassing compartment 34.

In the embodiments shown in FIGS. 4a and 4B, two degassing compartments 34 are associated with a respective main opening 31, 32, 33. Advantageously, these degassing compartments 34 are diametrically opposed to facilitate the evacuation of all bubbles formed in the corneal tissue 6. Of course, more than two (or less than two) degassing compartments (for example three, four, etc.) can be associated with each main opening 31, 32, 33.

The degassing compartments 34 can be made substantially circular to facilitate the manufacture (including demolding) of the spacer 3. However, other shapes can be provided for the degassing compartments (oblong, rectangular, etc.).

1.3. Peripheral Seal

The peripheral seal 4 ensures the lateral sealing of the device once the transparent plates 1, 2 are assembled, in particular at the edges 11, 21 of the first and second plates 1, 2.

Advantageously, the peripheral seal 4 is made of a biocompatible and sterilizable elastomer material, for example silicone-based.

Figure 5:
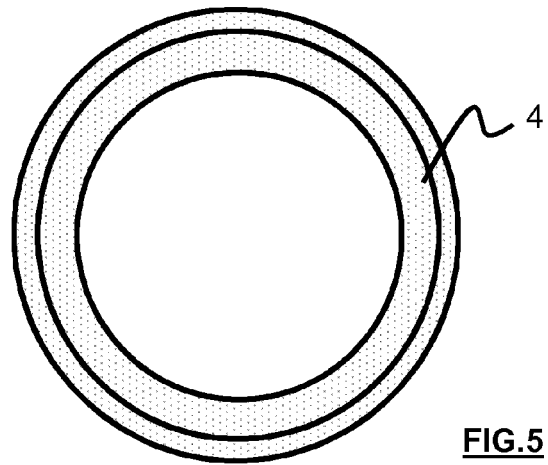
FIG. 5 is a top view of a peripheral seal of the holding device.
Figure 6:
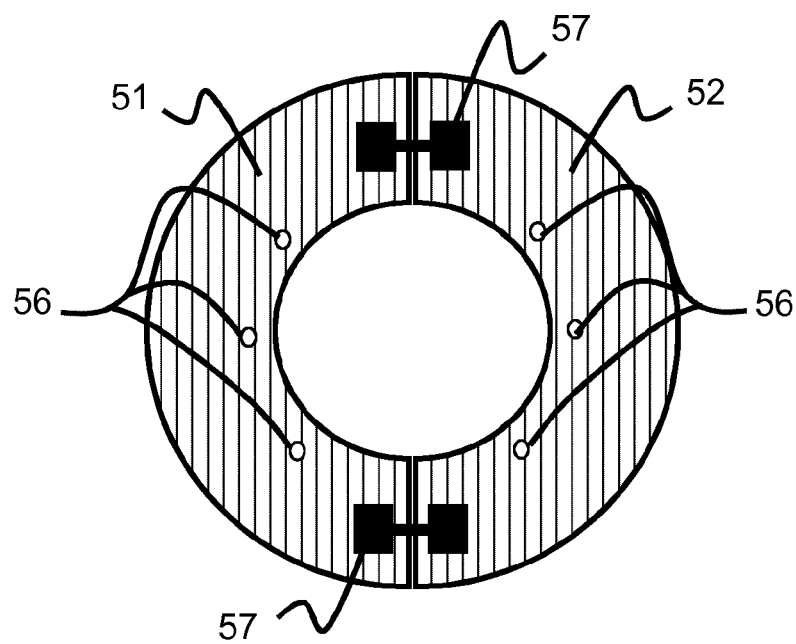
FIG. 6 is a top view of a locking system of the holding device.

In the embodiment shown in FIG. 5, the peripheral seal 4 is ring-shaped. However, it is quite obvious to the skilled person that the peripheral seal 4 can have other shapes (square, rectangular, triangular, etc.), in particular as a function of the shape of the first and second plates 1, 2.

The thickness of the peripheral seal 4 and the thickness of the spacer 3 define the distance between the first and second plates 1, 2, and thus the thickness mechanical stress applied to the corneal tissue 6 by said plates 1, 2. Seals 4 and spacers 3 of several thicknesses can be provided to adapt the thickness of the device to the thickness of the corneal tissue 6, or to specific user choices. In particular in an embodiment, the thickness of the peripheral seal (and/or of the spacer) can be comprised between 100 µm and 1800 µm, preferably between 400 µm and 1500 µm, and more preferably between 500 µm and 700 µm. This allows the first and second plates to be spaced at a distance that guarantees the mechanical stress of the anterior and posterior surfaces of the corneal tissue 6 in order to ensure that the corneal tissue 6 is locked in position in the holding device.

In a variant, the seal 4 and the spacer 3 can be made of an expandable and/or compressible material to accommodate different distances between the first and second plates 1, 2. In this case, the adjustment of this distance is provided by the locking system 51, 52 so that the first and second plates are spaced at a distance comprised between 100 µm and 1800 µm, preferably between 400 µm and 1500 µm, and more preferably between 500 µm and 700 µm.

1.4. Locking System

The locking system 51, 52 holds in position the assembly composed of the first and second plates 1, 2, the seal 4 and the optional spacer 3. It guarantees the stability of this assembly and allows it to be handled by the user without risk of unintentional opening.

The locking system 51, 52 is removable to allow:
insertion of the corneal tissue 6 into the device prior to cutting,
recovery of the fragments once the corneal tissue 6 has been cut.

With reference to FIG. 1, the locking system may comprise a frame intended to encircle the edges 11, 21 of the first and second plates 1, 2. The frame may be composed in two parts, in particular the frame may include first and second portions 51, 52.

Figure 7:
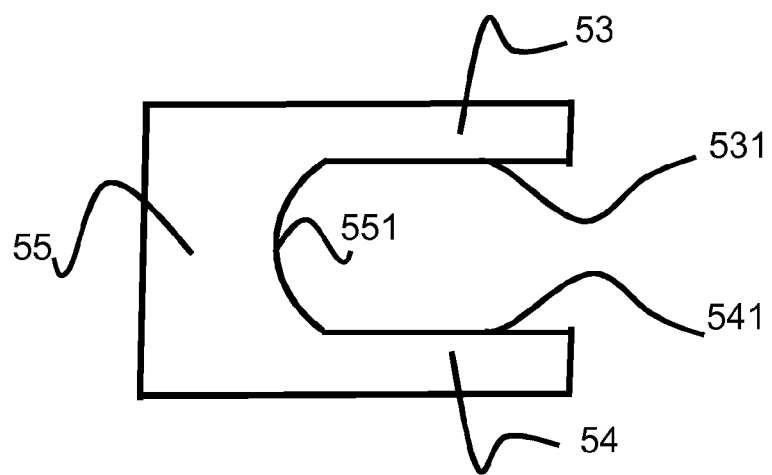
FIG. 7 is a sectional view of a portion of the locking system shown in FIG. 6.

Each portion 51, 52 consists for example of a halfcylinder including a central through-lumen extending along the longitudinal axis A-A' of the device. More precisely and with reference to FIG. 7, each portion comprises upper and lower annular trays 53, 54 and a side wall 55:
the inner face 531 of the upper tray 53 is intended to come facing the outer face of the first plate 1,
the inner face 541 of the lower tray 54 is intended to come facing the outer face of the second plate 2, and
the inner face 551 of the side wall 55 is intended to come facing the edges 11, 21 of the plates 1, 2 and the outer face of the seal 4.

The upper tray 53 and/or the lower tray 54 of each portion 51, 52 may comprise one (or more) hole(s) 56 for the passage of a clamping element—such as a screw with a threaded shank—allowing a force to be applied according to the longitudinal direction A-A' and tending to press the plates 1, 2 against the seal 4 and the spacer 3. This clamping element further makes it possible to set the desired distance between the first and second plates 1, 2 (and thus the mechanical stress applied to the corneal tissue 6).

The first and second portions 51, 52 may also comprise fastening means 57 to enable said portions to be joined together.

Figure 3:
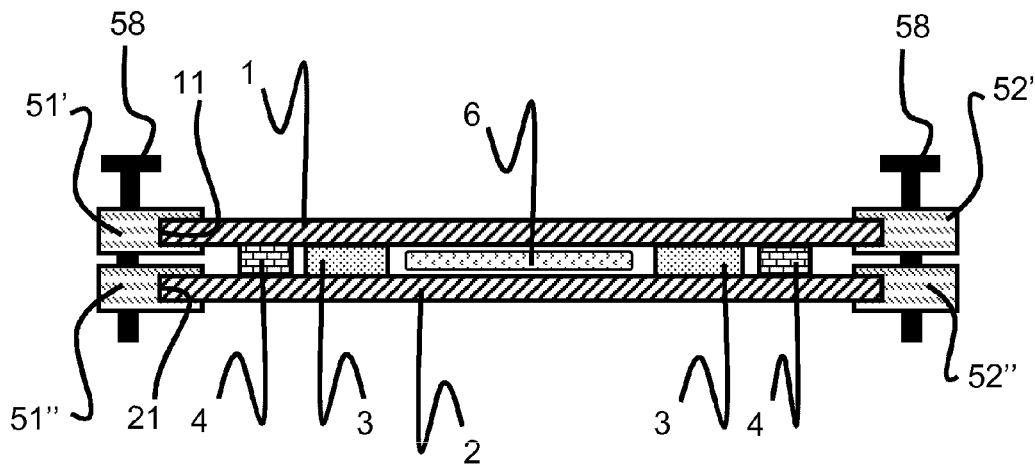
FIG. 3 is a sectional view of a variant embodiment of the holding device once assembled, FIG. 4A (single capacity) and 4B (dual capacity) are top views of examples of the spacer of the holding device.

In a variant and as shown in FIG. 3, the locking system can comprise first and second elementary frames:
the first elementary frame comprises first and second elementary portions 51', 52' intended to encircle the edge 11 of the first plate 1, and
the second elementary frame comprises first and second portions 51", 52" intended to encircle the edge 21 of the second plate 2.

In this case, the first and second elementary frames are joined together by means of a plurality of micrometric screws 58 making it possible to adjust the distance between the first and second elementary frames, and thus the distance between the first and second plates 1, 2, so that the distance between the first and second plates is comprised between 100 µm and 1800 µm, preferably between 400 µm and 1500 µm, and more preferably between 500 µm and 700 µm.

2. Principle of Operation

The principle of operation of the holding device described above is the following.

It is assumed that the various elements making up the holding device have been previously sterilized.

The user positions the second plate 2 on a support. She installs the spacer 3 on the second plate 2. She positions the peripheral seal 4 around the spacer 3.

Once these three elements are assembled, the user inserts the corneal tissue 6 into the main opening 31 of the spacer 3. A liquid or gel can be introduced into the main opening 31 (around the cornea) to improve radiation transmission (in particular to homogenize the refractive indices, for example).

The user then places the first plate 1 on the spacer 3 and the seal 4. The transparency of the first and second plates 1, 2 to the light allows the user to visually check the correct positioning of the corneal tissue 6 in the main opening 31.

The user then forces the first and second portions 51, 52 of the locking system around the edges 11, 21 of the first and second plates 1, 2. The user actuates the fastening means 57 of the first and second portions 51, 52 to join them together.

In an example embodiment with a locking system with adjustable distance by micrometric screws, the user then acts on the clamping element(s) to adjust the distance between the first and second plates 1, 2.

The holding device is then assembled: the corneal tissue 6 is constrained between the first and second plates 1, 2.

The holding device is fixed on a support facing an electromagnetic radiation source, optionally in a vertical position to facilitate the evacuation of gas bubbles (likely to form when cutting corneal tissue) toward the degassing compartment(s) 34.

The user then activates the electromagnetic radiation source to perform a plurality of cutting planes in the corneal tissue 6.

Once the cutting planes have been made, the user disengages the clamping elements and the fastening means 57. She takes off the locking system and removes the first plate 1. The treated corneal tissue 6 can then be retrieved.

3. Conclusions

The device described above allows the action of a photonics instrument—for example a cutting or treatment laser source—in ex vivo human or animal corneal tissue, passing through the epithelial (outer surface) and endothelial (inner surface) surfaces of the corneal tissue.

The device restrains the corneal tissue by constraining it between two plates transparent to electromagnetic radiation. This constraint:

keeps the corneal tissue immobile, even when the corneal tissue is subjected to light radiation, maintains the corneal tissue in a predefined shape (flat, concave or convex) as a function of the intended application.

The restraint of the corneal tissue by the device makes it possible to obtain a known and stable stressed position in XYZ. This position stability makes it possible to turn the device without loss of marks, to continue a cut initiated on one surface and finished on the other.

The mechanical stress applied to the corneal tissue by the two plates also facilitates the evacuation of gas bubbles formed during the light/cornea interaction (in particular during laser treatment which creates cavitation bubbles during plasma formation). In this respect, the degassing compartment(s) allow(s) gas bubbles to be stored outside the corneal tissue.

The device allows the preparation of the cornea under sterile and sealed (closed) conditions. It also allows the handling of the corneal tissue once treated in a non-sterile environment without deconditioning the cornea and without compromising its sterility.

The device allows for custom cutting of any shape within the corneal tissue (called fragment) using a horizontal, oblique, vertical or free-form cutting plane.

The reader will have understood that many modifications can be provided to the invention described above without materially losing the new teachings and advantages described here.

In particular, in the embodiments presented, the holding device comprises one or two housings, each intended to receive eye tissue. It is quite obvious to the skilled person that the device may comprise more than two housings (notably three, four, five, etc.).

Also, it is quite obvious to the skilled person that the device can be without spacers.

The invention claimed is:

1. A device for holding human or animal corneal tissue previously removed for photonic treatment thereof from electromagnetic radiation, wherein the holding device comprises:

a stack of elements along a longitudinal axis A-A' of the device, said stack comprising:
 a first plate transparent to electromagnetic radiation,
 a peripheral seal positioned on the first plate, wherein the peripheral seal extends around the corneal tissue, and
 a second plate transparent to electromagnetic radiation on the peripheral seal;

a locking system of the stack of elements, wherein the locking system presses the first and second plates against the corneal tissue and applies mechanical stress to the anterior and posterior faces of the corneal tissue, the locking system comprising:
 a frame having:
  a first semi-circular portion for surrounding a first half of an edge of the first plate and the second plate; and
  a second semi-circular portion for surrounding a second half of the edge of the first plate and the second plate.

2. The holding device according to claim 1, wherein the first and second plates are parallel, the distance between the first and second plates being comprised between 100 μm and 1800 μm, preferably between 400 μm and 1500 μm, and more preferably between 500 μm and 700 μm.

3. The holding device according to claim 1, wherein the thickness of the peripheral seal is comprised between 100 μm and 1800 μm, preferably between 400 μm and 1500 μm, and more preferably between 500 μm and 700 μm, said thickness of the seal defining the distance between the first and second plates representative of the mechanical stress applied to the corneal tissue by said plates.

4. The holding device according to claim 3, wherein the locking system of the stack of elements presses the first and second plates against the peripheral seal so as to space the first and second plates at a distance comprised between 100 μm and 1800 μm, preferably between 400 μm and 1500 μm, and more preferably between 500 μm and 700 μm.

5. The holding device according to claim 1, wherein the locking system further comprises at least one clamping element for clamping at least one of the first portion and the second portion, the at least one clamping element being able to:

induce on the first plate the application of a force parallel to the longitudinal axis A-A' and tending to move the first plate toward the second plate, induce on the second plate the application of a force parallel to the longitudinal axis A-A' and tending to move the second plate toward the first plate.

6. The holding device according to claim 5, wherein each portion of the frame includes an upper tray, a lower tray and a side wall between the upper and lower trays:

an inner face of the upper tray faces an outer face of the first plate, an inner face of the lower tray faces an outer face of the second plate, and an inner face of the side wall faces the edges of the plates and an outer face of the seal.

7. The holding device according to claim 6, wherein each clamping element is intended to cooperate with a respective hole in the upper tray and/or in the lower tray of the first and the second portions of the frame.

8. The holding device according to claim 7, wherein each clamping element is movable to adjust the distance between the first and second plates, said distance being comprised between 100 µm and 1800 µm, preferably between 400 µm and 1500 µm, and more preferably between 500 µm and 700 µm.

9. The holding device according to claim 6, wherein the first and second portions of the frame include fastening means to enable said portions to be joined together.

10. The holding device according to claim 1, which further comprises a spacer positioned between the first and second plates, the peripheral seal extending around the spacer.

11. The holding device according to claim 10, wherein the thickness of the spacer is comprised between 100 µm and 1800 µm, preferably between 400 µm and 1500 µm, and more preferably between 500 µm and 700 µm, said thickness of the spacer defining the distance between the first and second plates representative of the mechanical stress applied to the corneal tissue by said plates, said distance being comprised between 100 µm and 1800 µm, preferably between 400 µm and 1500 µm, and more preferably between 500 µm and 700 µm.

12. The holding device according to claim 11, wherein the spacer comprises at least one main opening defining, with the inner faces of the first and second plates, a housing intended to contain the corneal tissue.

13. The holding device according to claim 10, wherein the spacer comprises at least one degassing compartment.

14. The holding device according to claim 12, wherein the spacer comprises at least one degassing compartment, and wherein the spacer comprises at least one connecting channel extending between the main opening and the at least one degassing compartment for the delivery of gas bubbles formed in the corneal tissue.

* * * * *